United States Patent
Dubey et al.

(10) Patent No.: US 11,480,558 B2
(45) Date of Patent: Oct. 25, 2022

(54) METHOD AND DEVICE COMPRISING AN OPTICAL FIBER LOCATED INSIDE A CHANNEL FOR DETERMINING THE CONCENTRATION OF ANALYTE IN WHOLE BLOOD BASED ON CHANGE OF REFLECTED LIGHT WAVELENGTH

(71) Applicant: Siemens Healthcare Diagnostics Inc., Tarrytown, NY (US)

(72) Inventors: Satish Kumar Dubey, Bangalore (IN); Ashish Kumar Lal, Bangalore (IN); Vishal Manjanath Prabhu, Bangalore (IN); David Ledden, Elkhart, IN (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 489 days.

(21) Appl. No.: 16/621,009

(22) PCT Filed: Jun. 7, 2018

(86) PCT No.: PCT/US2018/036434
§ 371 (c)(1),
(2) Date: Dec. 10, 2019

(87) PCT Pub. No.: WO2018/231625
PCT Pub. Date: Dec. 20, 2018

(65) Prior Publication Data
US 2020/0200730 A1  Jun. 25, 2020

Related U.S. Application Data

(60) Provisional application No. 62/520,087, filed on Jun. 15, 2017.

(51) Int. Cl.
*G01N 33/49* (2006.01)
*G01N 21/05* (2006.01)
*G01N 21/552* (2014.01)
*G01N 21/03* (2006.01)

(52) U.S. Cl.
CPC ............. *G01N 33/49* (2013.01); *G01N 21/05* (2013.01); *G01N 21/552* (2013.01); *G01N 2021/0346* (2013.01); *G01N 2021/052* (2013.01)

(58) Field of Classification Search
CPC ........ G01N 33/49; G01N 21/55; G01N 21/05; G01N 2021/05
(Continued)

(56) References Cited

U.S. PATENT DOCUMENTS 5,650,846 A   7/1997  Yin et al.
6,268,910 B1  7/2001  Samsoondar et al.
(Continued)

FOREIGN PATENT DOCUMENTS

EP   2793015 A1    10/2014
JP   H09511065 A   11/1997
(Continued)

OTHER PUBLICATIONS

International Search Report and Written Opinion of International Application No. PCT/US2018/036434 dated Aug. 10, 2018.
(Continued)

*Primary Examiner* — Que Tan Le

(57) ABSTRACT

A method and a device for determining the concentration of an analyte in whole blood is disclosed. In one embodiment, the method includes generating a plasma layer in the whole blood sample. Furthermore, the method includes exposing the plasma layer to light. The method also includes capturing light reflected from the plasma layer. Additionally, the method includes analyzing the reflected light to determine the concentration of the analyte.

16 Claims, 3 Drawing Sheets

(58) Field of Classification Search
USPC .............................................. 250/221, 559.4
See application file for complete search history.

(56) References Cited

U.S. PATENT DOCUMENTS

| | | | |
|---|---|---|---|
| 6,366,726 | B1 | 4/2002 | Wash et al. |
| 10,852,295 | B2 * | 12/2020 | Schonbrun ............. G01N 21/25 |
| 2005/0249633 | A1 | 11/2005 | Blatt et al. |
| 2006/0204403 | A1 | 9/2006 | Federas |
| 2008/0240543 | A1 | 10/2008 | Budach et al. |
| 2014/0252214 | A1 | 9/2014 | Holzki et al. |
| 2014/0262831 | A1 | 9/2014 | Balasubramanian et al. |

FOREIGN PATENT DOCUMENTS

| | | |
|---|---|---|
| JP | 2004505291 A | 2/2004 |
| JP | 2013164372 A | 8/2013 |
| WO | 9527208 A1 | 10/1995 |
| WO | 2016193066 A1 | 12/2016 |
| WO | 2017200907 A1 | 11/2017 |

OTHER PUBLICATIONS

European Search Report and Search Opinion of European Application No. 18817299.3 dated May 19, 2020.
Sakota et al., "Simultaneous determination of hemolysis and hematocrit in extracorporeal circulation by plasma surface reflectance spectroscopy", 2013, 35th Annual International Conference of the IEEE Engineering in Medicine and Biology Society (EMBC), pp. 6764-6767.

* cited by examiner

US 11,480,558 B2

METHOD AND DEVICE COMPRISING AN OPTICAL FIBER LOCATED INSIDE A CHANNEL FOR DETERMINING THE CONCENTRATION OF ANALYTE IN WHOLE BLOOD BASED ON CHANGE OF REFLECTED LIGHT WAVELENGTH

This application claims priority to U.S. Provisional Application No. 62/520,087, filed Jun. 15, 2017, the disclosure of which is hereby incorporated by reference in its entirety.

FIELD OF TECHNOLOGY

The present disclosure relates to the field of analysis of whole blood and more particularly to the field of determining the concentration of analyte in whole blood.

BACKGROUND

Hemolysis is a phenomenon wherein the blood cells rupture in whole blood, releasing their content into the blood plasma. This condition may occur due to various reasons such as immune reactions, infections, and medications. Hemolysis may occur within the body of an individual or after the blood has been extracted out of the body. A major cause of hemolysis is the pre-analytical steps of blood sample handling, including collection of the blood sample from the body of an individual. As a result, the individual may have a hemolytic condition, such as sickle cell anemia. During hemolysis, the composition of the blood plasma is altered because of the contents of the blood cells spilling into the blood plasma. If the composition of the blood plasma is altered beyond a certain threshold, the blood sample is flagged for hemolysis. If the composition of the blood plasma is altered beyond a higher threshold, the blood sample may become incapable of further use and therefore has to be rejected. Therefore, the object of the invention is to provide a method to determine concentration of analytes, particularly extracellular hemoglobin, in a whole blood sample.

SUMMARY

A method for determining the concentration of an analyte in whole blood sample is disclosed. In one aspect of the invention, the method includes generating a plasma layer in the whole blood sample. The method also includes exposing the plasma layer to light. Furthermore, the method includes capturing light reflected from the plasma layer. Additionally, the method also includes analyzing the reflected light to determine the concentration of the analyte.

In another aspect, a device for determining the concentration of an analyte in whole blood sample includes a channel configured to carry whole blood; a light source configured to direct light on the channel; and a measuring unit. The measuring unit is configured to capture light reflected from the surface of the channel. Furthermore, the measuring unit is configured to compute a change in wavelength of the reflected light, wherein the change is the wavelength of the reflected light is proportional to the concentration of the analyte in the whole blood.

This summary is provided to introduce a selection of concepts in a simplified form that are further described below in the following description. It is not intended to identify features or essential features of the claimed subject matter. Furthermore, the claimed subject matter is not limited to implementations that solve any or all disadvantages noted in any part of this disclosure.

BRIEF DESCRIPTION OF THE DRAWINGS

The present invention is further described hereinafter with reference to illustrated embodiments shown in the accompanying drawings, in which.

DETAILED DESCRIPTION

Figure 1:
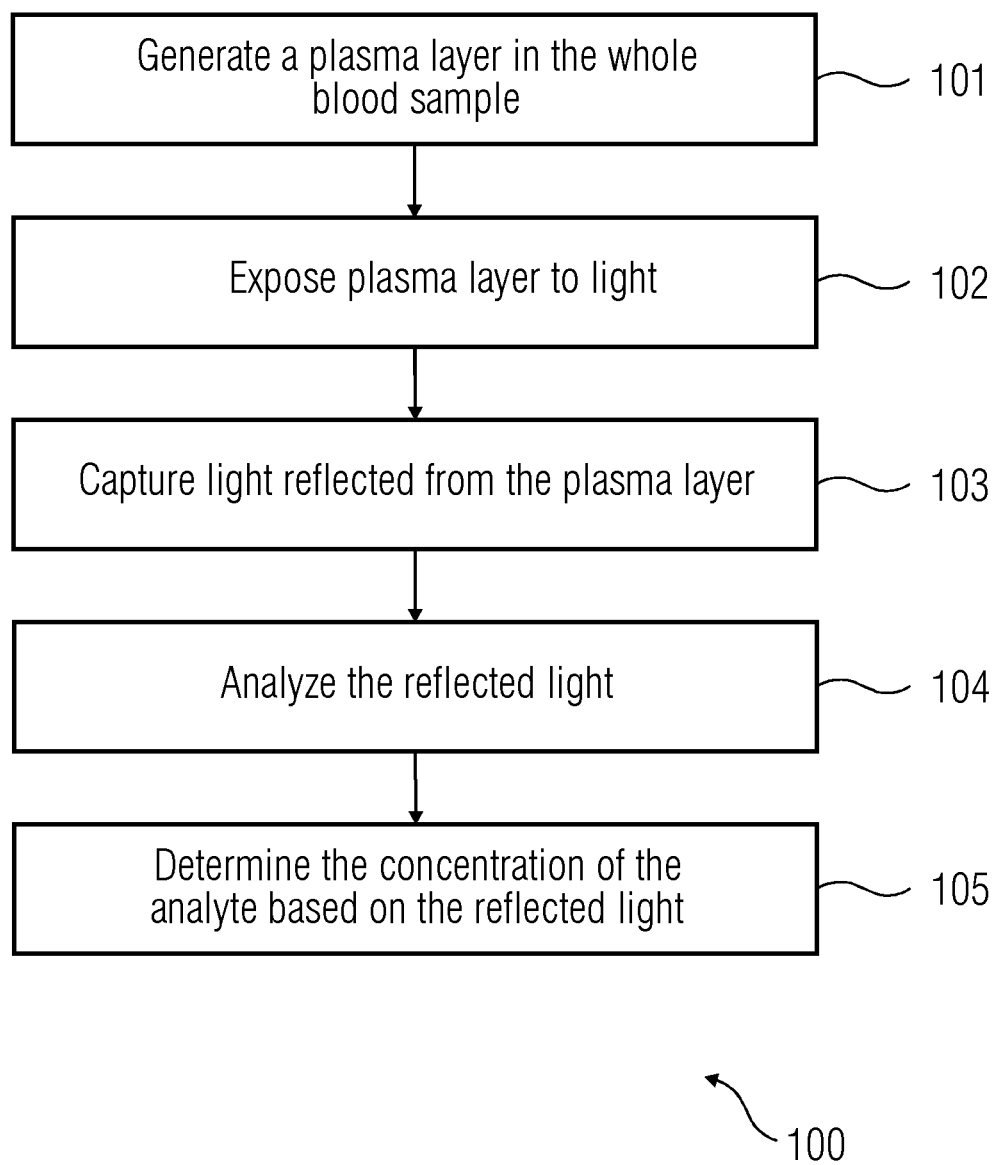
FIG. 1 illustrates a flowchart of an exemplary method of determining the concentration of an analyte in whole blood.

Hereinafter, embodiments for carrying out the present invention are described in detail. The various embodiments are described with reference to the drawings, wherein like reference numerals are used to refer to like elements throughout. In the following description, for purpose of explanation, numerous specific details are set forth in order to provide a thorough understanding of one or more embodiments. It may be evident that such embodiments may be practiced without these specific details. In other instances, well known materials or methods have not been described in detail in order to avoid unnecessarily obscuring embodiments of the present disclosure. While the disclosure is susceptible to various modifications and alternative forms, specific embodiments thereof are shown by way of example in the drawings and will herein be described in detail. It should be understood, however, that there is no intent to limit the disclosure to the particular forms disclosed, but on the contrary, the disclosure is to cover all modifications, equivalents, and alternatives falling within the spirit and scope of the present disclosure.

Optical detection of hemolysis in whole blood can be challenging because of high interference from blood cells, specifically red blood cells (RBCs). Separating blood plasma from whole blood in order to detect hemolysis is time consuming and arduous. Therefore, there exists a need for a method that can detect hemolysis which does not require separation of blood plasma from whole blood, which is faster and cost efficient.

FIG. 1 illustrates a flowchart of an embodiment of an exemplary method 100 of determining the concentration of an analyte present in whole blood. The method 100 includes step 101 of generating a plasma layer in the whole blood sample. The plasma layer in the whole blood sample can be generated by passing the sample through a fluidic channel, for example, a microfluidic channel. The fluidic channel may be made of a transparent medium, for example, glass and includes an outer surface and an inner surface. When whole blood flows through a channel with a narrow diameter, the blood cells migrate to the center of the channel, thereby generating a layer of plasma at the walls of the channel. This phenomenon is termed as 'Fahraeus effect'. Fahraeus effect results in decrease in the average concentration of red blood cells when the diameter of the channel through which the blood flows decreases. During hemolysis, the red blood cells rupture, thereby resulting in spilling of the contents of the red blood cells, including analytes such as hemoglobin into the plasma.

By utilizing the Fahraeus effect, the concentration of the red blood cells can be decreased along the walls of the microfluidic channel. Therefore, the plasma layer generated along the walls of the microfluidic channel is devoid of red blood cells. Thus, the concentration of analytes, such as hemoglobin, in the plasma layer can be effectively determined without interference from the blood cells.

At step 102, the generated plasma layer is exposed to light. The plasma layer is irradiated with light of a wavelength in the range between 400-750 nm at an angle greater than the total internal reflection critical angle. The total internal reflection critical angle is the angle of incidence for which the light totally reflects from an interface. The incident light passes through the medium of the microfluidic channel and interacts with the plasma layer generated at the walls of the channel. In an embodiment, an index matching substance may be used along with the microfluidic channel so as to ensure that the irradiated light is reflected off the plasma layer and not the surface of the microfluidic channel. Examples of index matching substances include fluids and solids. Examples of index matching fluids include, but are not limited to, paraffin, glycerin, and sugar solution. Examples of index matching solids include, but are not limited to, glass. In an alternate embodiment, the microfluidic channel may also be pasted on to another piece of glass. The refractive index of the adhesive used between the microfluidic channel and the piece of glass should be the same as the refractive index of glass. Alternatively, the microfluidic channel may also be etched on a glass surface using techniques well known in the state of the art.

Figure 2A:
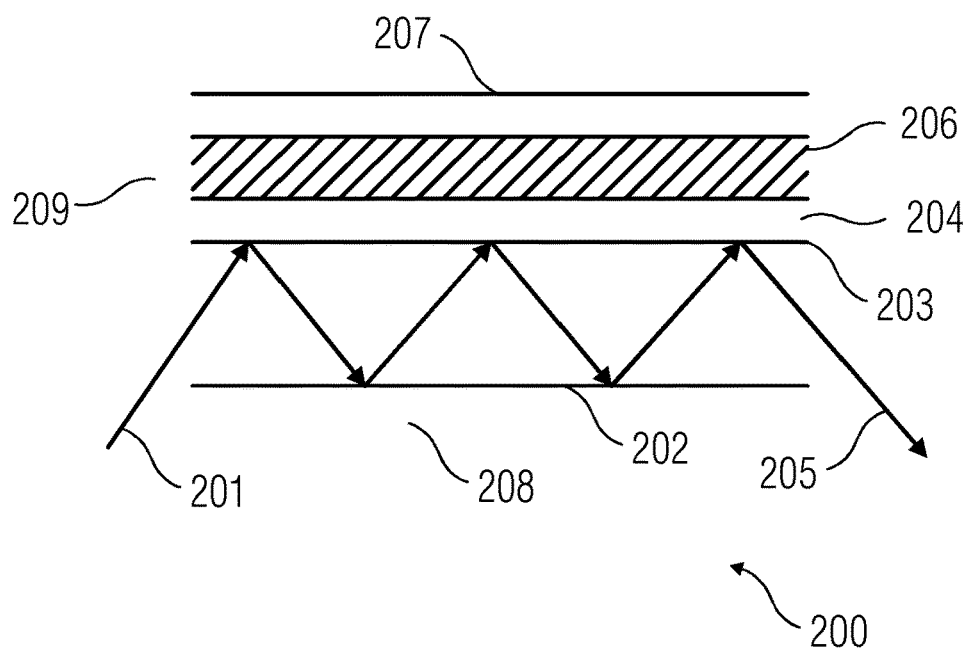
FIG. 2A illustrates a side view of an illustrative device which can be used to determine the concentration of an analyte in plasma.
Figure 2B:
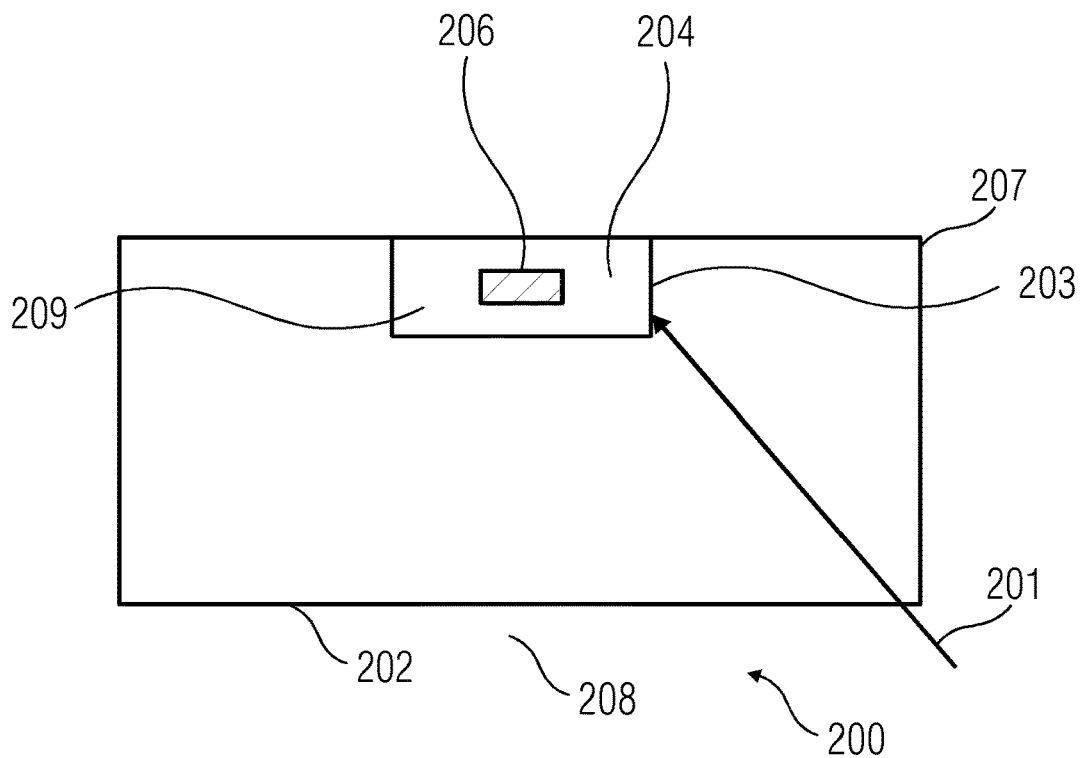
FIG. 2B illustrates a vertical cross sectional view of the illustrative device which can be used to determine the concentration of an analyte in plasma.

The irradiated light may be reflected multiple times by the plasma layer, as depicted in FIG. 2A. FIG. 2A illustrates a side view of an illustrative device 200 which can be used to determine the concentration of an analyte in plasma. The device is a fluidic device, such as a microfluidic device. In the embodiment, a channel 209 is etched on a first layer of transparent material 208. The channel 209 may be, for example, a microfluidic channel. The first layer of transparent material 208 includes an outer surface 202 and an inner surface 203. The microfluidic channel 209 is defined by the inner surface 203 of the transparent material 208. A second layer of transparent material 207 is placed over the first layer of transparent material 208. The layers of transparent material 207, 208 may be made of index matching substances, for example, glass. The microfluidic channel 209 contains a whole blood sample. Using the Fahraeus Effect, the red blood cells 206 migrate to the center of the microfluidic channel 209, thereby generating a cell-free plasma layer 204 along the inner surface 203 of the microfluidic channel 209. FIG. 2B illustrates a vertical cross sectional view of the illustrative device 200. The red blood cells 206 gather at the center of the microfluidic channel 209 using Fahraeus Effect. A layer of plasma 204 is generated around the red blood cells. The irradiated light 201 enters the glass surface and interacts with the plasma layer 204 at the inner surface 203 of the micro fluidic channel 209. On hitting the inner surface 203 of the microfluidic channel 209, the light can be reflected multiple times between the inner and outer surfaces of the microfluidic channel 209. The critical angles for total internal reflection are different for the air-glass interface and glass-plasma interface. The chosen incident angle in FIGS. 2A and 2B is greater than the critical angles for the air-glass interface and glass-plasma interface to ensure multiple reflections. At step 103, the reflected light 205 is captured. The reflected light 205 may be captured using a spectrophotometer. At step 104, the captured reflected light 205 is analyzed to detect a change in the wavelength. The wavelength of the reflected light 205 may vary according to the concentration of the analyte in the separated plasma layer 204. At step 105, the concentration of the analyte is determined based on the wavelength of the reflected light 205.

Figure 3A:
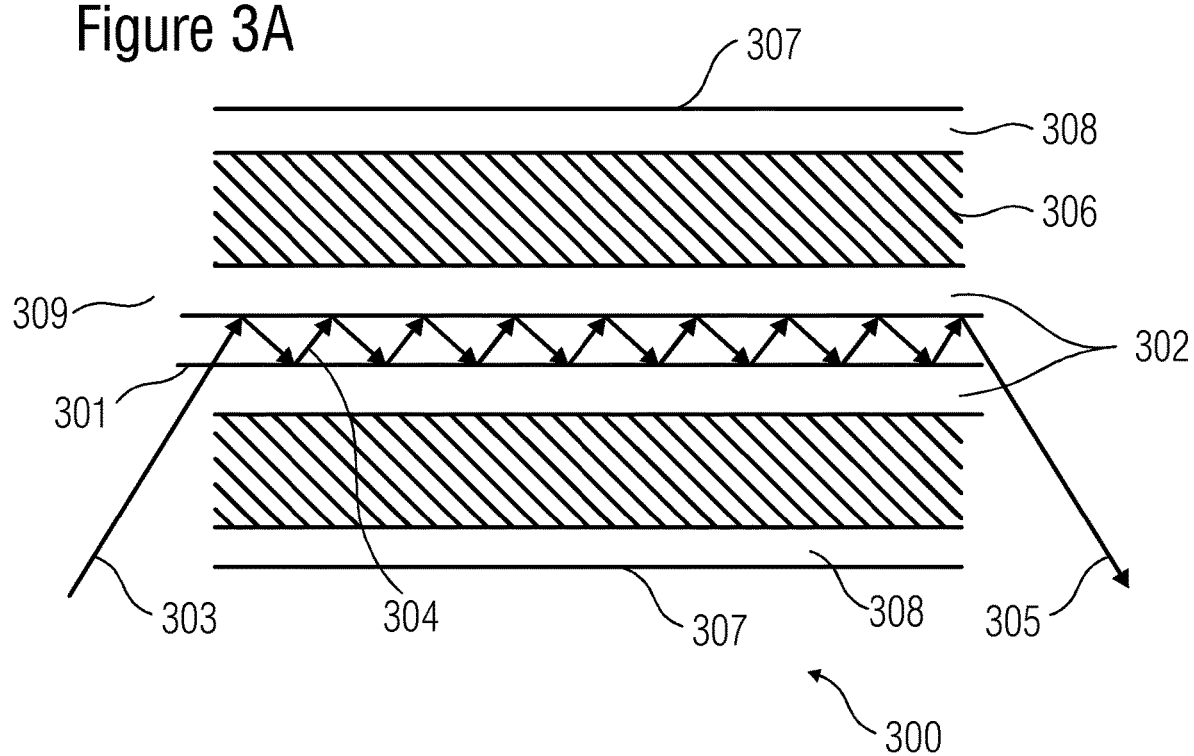
FIG. 3A illustrates a side view of another embodiment of an illustrative device which can be used to determine the concentration of an analyte in plasma.
Figure 3B:
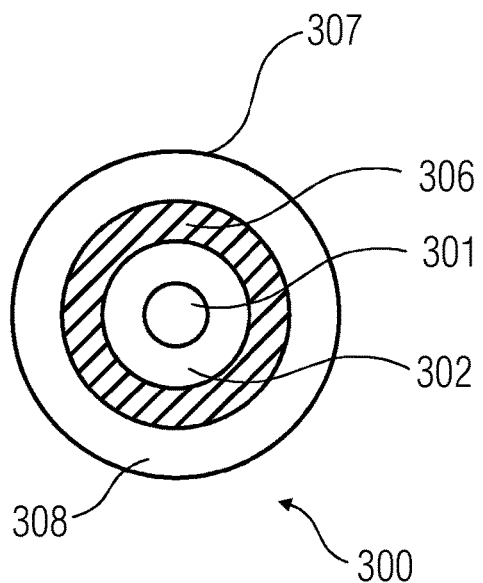
FIG. 3B illustrates a schematic representation of a cross sectional view of the illustrative device which can be used to determine the concentration of analyte in plasma.

FIG. 3A illustrates a side view of another embodiment of an illustrative device 300 which can be used to determine the concentration of an analyte in plasma. In the embodiment, the device 300 includes an optical fiber 301 that is located within the channel 309. The channel 309 may be a microfluidic channel. In illustrative embodiments, the optical fiber 301 may be located in or towards the center of the channel 309 or adjacent to the interior surface of the channel 309. The whole blood sample flows through the microfluidic channel 309 at a constant flow rate. The rate at which the whole blood flows through the microfluidic channel 309 may be within a range at which Fahraeus Effect can be effectively achieved. The optical fiber 301 may be a thin, transparent fiber of glass or plastic and is without cladding. FIG. 3B illustrates a vertical cross sectional view of the device 300, having a channel 309 with the optical fiber 301 located in the center. The channel 309 is defined by the outer surface 307 of the device 300. The optical fiber 301 is placed parallel to the central axis of the microfluidic channel 309. The central axis of the microfluidic channel 309 is parallel to the flow path of the whole blood in the microfluidic channel 309. In one embodiment, the optical fiber 301 may be placed parallel to the central axis such that the optical fiber 301 is not in contact with the inner surface of the microfluidic channel 309. Due to the placement of the optical fiber 301 inside the microfluidic channel 309, a layer of cell-free plasma 302 is generated using Fahraeus Effect, around the optical fiber 301. An additional layer of plasma 308 may also be formed along the walls of the microfluidic channel 309 using Fahraeus Effect. In between cell-free plasma layers 302 and 308, a layer of red blood cells 306 is formed. In the embodiment illustrated in FIGS. 3A and 3B, this layer of red blood cells 306 extends along, and encircles, the optical fiber. In an alternate embodiment, the optical fiber 301 may be placed in contact with the inner surface of the microfluidic channel 309. When light 303 is irradiated into the optical fiber 301, the light 303 interacts with the separated layer of plasma and gets reflected. Within the optical fiber 301, the light 303 may be reflected multiple times 304 between the surfaces of the optical fiber 301. The phenomenon of multiple reflections 304 of the irradiated light 303 allows for signal amplification and therefore enables accurate determination of the concentration of the analyte present in the whole blood sample. Therefore, the reflected light 305 is further captured by the spectrophotometer and a change in the wavelength of the reflected light 305 is detected. Based on the wavelength of the reflected light 305, the concentration of the analyte in the whole blood sample is determined, wherein the concentration of the analyte is proportional to the wavelength of the reflected light 305.

The method 100 enables measurement of hemolysis in the whole blood sample in a microfluidic environment. Therefore, the sample volume requirements are low. Furthermore, as no additional reagents are required for the determination of the concentration of the analyte, the method is cost effective. The whole blood sample may also be retrieved for further analysis or downstream processing once the process of determination of the concentration of the analyte is completed.

What is claimed is:

1. A method of determining the concentration of an analyte in a whole blood sample, the method comprising:
   flowing a whole blood sample through a channel;
   generating a plasma layer in the channel, the plasma layer being devoid of blood cells;
   directing light at the plasma layer;
   passing the light through an optical fiber located inside the channel and extending in parallel with the channel to reflect the light off of the plasma layer multiple times;
   capturing light reflected off of the plasma layer; and
   analyzing the reflected light to determine the concentration of the analyte.

2. The method of claim 1, wherein when the whole blood sample flows through the channel the blood cells migrate to the center of the channel thereby creating a plasma layer at the inner surface of the channel.

3. The method of claim 1, wherein in generating a plasma layer in the whole blood sample, the method comprises using the optical fiber inside the channel, wherein the whole blood surrounds the optical fiber as it flows through the channel.

4. The method of claim 1, wherein the light is directed at the plasma layer at an angle sufficient to cause a reflection off of the plasma layer.

5. The method of claim 4, further comprising redirecting the reflected light back to the plasma layer.

6. The method of claim 1, wherein the light is directed at the inner surface of the optical fiber.

7. The method of claim 1, wherein in analyzing the reflected light to determine the concentration of the analyte, the method comprises:
   detecting a change in the wavelength of the reflected light; and
   determining the concentration of the analyte in the whole blood sample based on the wavelength of the reflected light.

8. The method of claim 1, wherein the reflected light is captured using a spectrophotometer.

9. The method of claim 1, wherein the analyte is hemoglobin.

10. A device for determining the concentration of an analyte in a whole blood sample, the device comprising:
    a channel configured to carry whole blood;
    a light source configured to direct light on the channel;
    an optical fiber through which the light passes and is reflected multiple times to form reflected light, the optical fiber being located inside the channel and extending in parallel with the channel; and
    a measuring unit configured to:
      capture the reflected light exiting from the channel; and
      compute a change in wavelength of the reflected light, wherein the change in the wavelength of the reflected light is proportional to the concentration of the analyte in the whole blood.

11. The device of claim 10, wherein when the whole blood is flown through the channel, the blood cells migrate to the center of the channel thereby creating a plasma layer at the inner surface of the channel.

12. The device of claim 10, wherein the channel is a fluidic channel etched on a transparent medium.

13. The device of claim 10, wherein the channel is a tubular structure made of a transparent medium.

14. The device of claim 13, wherein the whole blood surrounds the optical fiber as it flows through the channel.

15. The device of claim 10, wherein the light is directed at the plasma layer at an angle sufficient to cause a reflection off of the plasma layer.

16. The device of claim 10, wherein the measuring unit is a spectrophotometer.

* * * * *